United States Patent
Kolberg (10) Patent No.: US 7,239,924 B2
(45) Date of Patent: Jul. 3, 2007

(54) ELECTRODE LINE

(75) Inventor: Gernot Kolberg, Berlin (DE)

(73) Assignee: BIOTRONIK GmbH & Co., KG, Berlin (DE)

(*) Notice: Subject to any disclaimer, the term of this patent is extended or adjusted under 35 U.S.C. 154(b) by 388 days.

(21) Appl. No.: 10/883,030

(22) Filed: Jun. 30, 2004

(65) Prior Publication Data

US 2005/0004640 A1   Jan. 6, 2005

(30) Foreign Application Priority Data

Jul. 4, 2003   (DE) ............................. 103 31 106

(51) Int. Cl.
*A61N 1/05* (2006.01)

(52) U.S. Cl. ..................... 607/126; 600/375; 600/381

(58) Field of Classification Search ............... 607/126, 607/128; 600/375, 381
See application file for complete search history.

(56) References Cited

U.S. PATENT DOCUMENTS

| | | | |
|---|---|---|---|
| 4,407,303 A * | 10/1983 | Akerstrom | 607/126 |
| 4,716,888 A * | 1/1988 | Wesner | 607/126 |
| 5,549,109 A * | 8/1996 | Samson et al. | 600/381 |
| 5,951,597 A | 9/1999 | Westlund et al. | |
| 5,954,761 A | 9/1999 | Machek et al. | |
| 6,304,786 B1 * | 10/2001 | Heil et al. | 607/126 |
| 6,551,278 B1 * | 4/2003 | Geitz | 604/131 |
| 2003/0149331 A1 * | 8/2003 | Geitz | 600/4 |
| 2004/0230279 A1 * | 11/2004 | Cates et al. | 607/126 |
| 2005/0171588 A1 * | 8/2005 | Wahlstrom et al. | 607/126 |

FOREIGN PATENT DOCUMENTS

EP   0 653 223   11/1993

* cited by examiner

*Primary Examiner*—Carl Layno
*Assistant Examiner*—Yun Haeng Lee
(74) *Attorney, Agent, or Firm*—Hahn Loeser & Parks, LLP; David J. Muzilla (57) ABSTRACT

Certain embodiments of the present invention concern an implantable electrode line having a proximal and a distal end, an outer electrode line surface and an electrode line longitudinal axis. The implantable electrode line is characterized in that the electrode line in the region of the distal end has a surface region with a microstructure, the surface region being provided for lateral contact with a vessel wall and being arranged at a spacing relative to the distal end which measures a plurality of electrode line diameters. The microstructure is formed by a plurality of microstructure elements which are arranged on the electrode line surface and which are distributed over the surface region both in the longitudinal direction and also in the peripheral direction and which have a component extending radially, wherein the microstructure elements are of a radial extent which is a fraction of the electrode line diameter. The microstructure elements are adapted, upon contact with a vessel wall, to counteract displacement of the electrode line along the electrode line longitudinal axis.

6 Claims, 6 Drawing Sheets

ELECTRODE LINE

TECHNICAL FIELD

Certain embodiments of the present invention relate to implantable electrode lines. More particularly, certain embodiments of the present invention relate to an implantable electrode line having a proximal and distal end, an outer electrode line surface and an electrode line longitudinal axis.

BACKGROUND OF THE INVENTION

Electrode lines, for example for cardiac pacemakers, suffer from the problem of electrode dislocations. Previous solutions for fixing an electrode line in the heart and in vessels are for example pre-shaped electrode lines which brace the electrode in vessels. Also known are helixes or screws which are disposed at the distal end of the electrode line on the electrode and which are adapted to fix the electrode to a myocardium by screwing therein. Also known are openings in the distal region of an electrode line, which are adapted to anchor the electrode line in the trabecula arrangement of a cardiac chamber.

The state of the art also includes hooks which are disposed at the distal end or on the electrode line and which are adapted to fix the electrode line to the myocardium.

The applicants' patent application WO97/31678 describes an electrode arrangement having a ventricular electrode which has hook-shaped fixing means at the distal end of the electrode.

DE 69430417 T2 discloses an electrode system in which the electrode line is of a flexible nature in order to form a loop between the atrial electrode and the ventricular electrode. In the proximity of the atrial electrodes that electrode line has a first passive fixing device in the form of hooks and in the proximity of the ventricular electrodes at the distal end it has a fixing device with two hooks.

Further limitations and disadvantages of conventional, traditional, and proposed approaches will become apparent to one of skill in the art, through comparison of such systems with the present invention as set forth in the remainder of the present application with reference to the drawings.

SUMMARY OF THE INVENTION

In accordance with an embodiment of the present invention, an implantable electrode line is provided which permits secure fixing of the electrode line in the heart and in vessels.

Such an embodiment is attained by an electrode line of the kind set forth in the opening part of this specification, which in the region of the distal end has at least one surface region with a microstructure, the surface region being provided for lateral contact with a vessel wall and being arranged at a spacing relative to the distal end which measures a plurality of electrode line diameters. The microstructure is formed by a plurality of microstructure elements which are arranged on the electrode line surface and which are distributed over the surface region both in the longitudinal direction and also in the peripheral direction and which extend with a radial directional component, preferably outwardly. The microstructure elements are of a radial extent which is a fraction of the electrode line diameter and are adapted, upon contact with a vessel wall, to counteract displacement of the electrode line along the electrode line longitudinal axis.

The advantage of such an electrode line is that many microstructure elements which measure a fraction of the electrode line diameter and which are distributed on a surface region of the electrode line afford a greater degree of adhesion than for example in the case of an electrode line which has only one or some hooks at the surface for fixing the electrode line.

In an embodiment of the present invention, the microstructure elements are in the form of microbristles, wherein the microbristles are arranged at a predetermined angle relative to the electrode line surface. The angle can be for example 90°. This advantageously provides that the electrode line is secured against longitudinal axial displacement equally in the direction of the proximal end and also in the direction of the distal end.

In a further embodiment, the microbristles are arranged in parallel relationship with the electrode line longitudinal axis, and in a particularly preferred feature the microbristles are oriented with a directional component facing towards the proximal end of the electrode line. This advantageously provides that the electrode line can be easily introduced in the implantation procedure and an increased level of resistance to displacement of the electrode line towards the proximal end is afforded by the orientation towards the proximal end. As an alternative to this embodiment a microstructured surface region may have both microstructure elements which are oriented with a directional component facing towards the proximal end and also such microstructure elements which are oriented with a directional component facing towards the distal end of the electrode line. Preferably the microbristles are oriented along the longitudinal axis of the electrode line alternately with a proximal and a distal directional component. That advantageously provides for fixing of the electrode line in respect of displacement along the longitudinal axis of the electrode line, both in a direction towards the proximal end of the electrode line and also in a direction towards the distal end thereof.

In another alternative embodiment of the present invention, the microbristles are arranged at a predetermined angle relative to the electrode line surface and are each oriented in mutually parallel relationship at a predetermined angle relative to the longitudinal axis of the electrode line. In this embodiment the microbristles are preferably oriented with a directional component facing towards the proximal end of the electrode line. That advantageously provides that the electrode line can be screwed into a vessel by rotation about the longitudinal axis in the peripheral direction. Preferably the bristles are adapted to bear flat against the electrode surface in the screwing-in operation. A rotational movement in opposite relationship to the screwing-in direction provides for fixing of the electrode line, repeated rotational movement in the screwing-in direction causes release of the electrode line.

Alternatively the microstructure elements are in the form of knobs which are adapted to cling to a vessel wall by adhesion. For that purpose the knobs preferably have a flat adhesion surface which is arranged perpendicularly to the radial direction of the electrode line. When coming into contact with a suitable pressure against a vessel wall, a sufficiently thin film of moisture can be produced between the adhesion surface and the vessel wall. That produces adhesion forces which fix the electrode line to the vessel wall.

In a further preferred feature the knobs are in the form of suction cups. For that purpose, instead of the flat adhesion surface, the knobs may have a concavely shaped adhesion surface.

In another embodiment the microstructure elements are in the form of scales with a scale edge. Preferably the scales are arranged at a predetermined angle, further preferably an acute angle, relative to the electrode line surface, in such a way that the scale edge is spaced from the surface of the electrode line. In a further preferred feature the scales are arranged in such a way that at least one edge portion of the scale edge has an orientational component extending perpendicularly to the longitudinal axis of the electrode line. This advantageously provides that, on coming into contact with a vessel wall, the electrode line is easily displaceable in one direction along the longitudinal axis of the electrode line while in the direction opposite thereto, by virtue of the scale edges engaging into the vessel wall, there is an increased level of resistance to longitudinal axial displacement.

In a further embodiment, the scales have at least one prong or tooth at the scale edge. That prong can advantageously engage into the vessel wall, in addition to the scale edge, and thus provide a further increased level of resistance to longitudinal axial displacement.

The microstructure elements can be disposed on or shaped from the surface of the electrode line. Preferably the microstructure is produced in a microstereolithographic process, for example by deposition on a substrate. The substrate can be applied to the electrode line surface or may be formed by the electrode line surface itself. Alternatively a surface region with a microstructure may also be produced by a microstereolithographically produced form.

An electrode line may have one or more surface regions with a microstructure, in which respect an embodiment or a combination of various embodiments of microstructure elements such as for example microbristles, scales, knobs or the embodiments of microstructure elements illustrated in the Figures can be implemented on just one electrode line.

Suitable materials for the electrode line are for example polytetrafluoroethylene (PTFE), silicone, polyimide, ethylene chlorotrifluoroethylene, ethylene tetrafluoroethylene (ETFE), polypropylene or polyurethanes. The microstructures can be produced jointly with the electrode line or a portion of the electrode line in an injection molding process, in which respect the microstructures can be appropriately incorporated in an injection molding mold.

For easy introduction of the electrode line into a lumen, an electrode line may have a longitudinally axially displaceable sheath which can be arranged on the electrode line in such a way as to cover the microstructure and, in the situation of use, to release the microstructure by retraction in a proximal direction.

These and other advantages and novel features of the present invention, as well as details of an illustrated embodiment thereof, will be more fully understood from the following description and drawings.

BRIEF DESCRIPTION OF SEVERAL VIEWS OF THE DRAWINGS

The invention will now be described in greater detail with reference to the Figures.

DETAILED DESCRIPTION OF THE INVENTION

Figure 1:
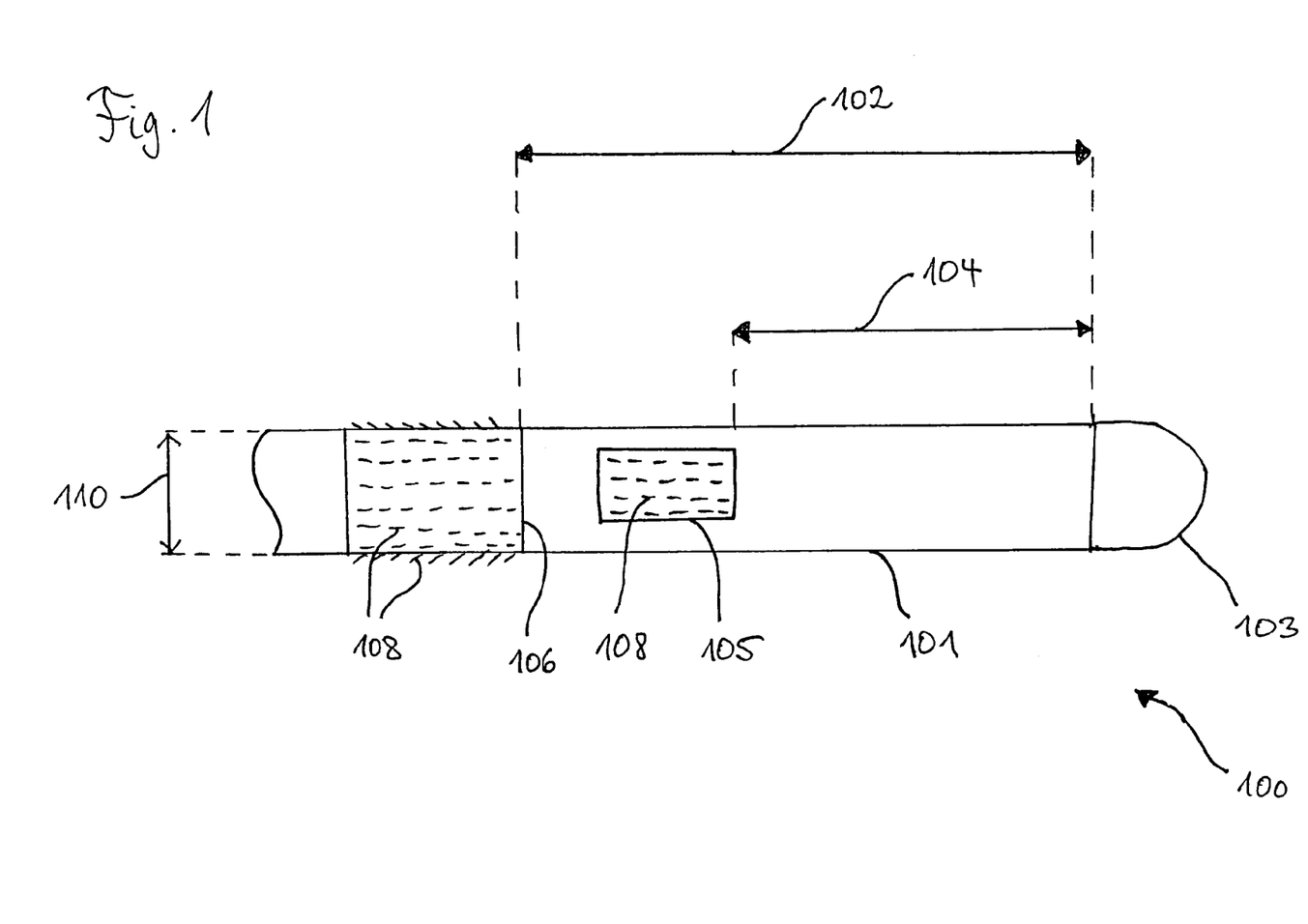
FIG. 1 shows the distal end of an electrode line having an electrode line surface and surface regions which each have a respective microstructure.

FIG. 1 diagrammatically shows the distal end of an electrode line 100 having an electrode line surface 101 and surface regions 105 and 106 which each have a respective microstructure. The surface region 105 is arranged at a spacing 104 from an electrode 103 disposed at the distal end of the electrode line. The surface region 105 with a microstructure occupies only a part of the surface of the electrode line, in the peripheral direction. In this example, the drawing also shows a peripherally extending surface region 106 which covers the outer electrode line surface 101 over the entire peripheral direction. In this embodiment the surface region 106 is arranged at a spacing 102 from the electrode 103 at the distal end. FIG. 1 shows two alternative configurations of surface regions—peripherally extending therearound and not extending therearound—jointly on one electrode line. An electrode line in accordance with the invention may have at least one surface region 106 extending entirely therearound in the peripheral direction of the electrode line or at least one surface region 105 which does not extend entirely therearound.

As an alternative thereto, an electrode line in accordance with the invention may have a plurality of surface regions 106 extending entirely therearound in the peripheral direction of the electrode line or a plurality of surface regions 105 which do not extend entirely therearound. A combination of surface regions 106 extending entirely around the electrode line and surface regions 105 which do not extend entirely therearound, on an electrode line, afford various alternative configurations which are not illustrated here. The spacings 102 and 104 may both amount to several electrode line diameters 110 and are diagrammatically illustrated in this example. The surface regions 106 and 105 have a microstructure, the microstructure being formed by a plurality of microstructure elements which are arranged on the surface of the electrode line and which are distributed over the surface region both in the longitudinal direction and also in the peripheral direction. Various embodiments of microstructure elements are illustrated hereinafter in FIG. 2.

Figure 2:
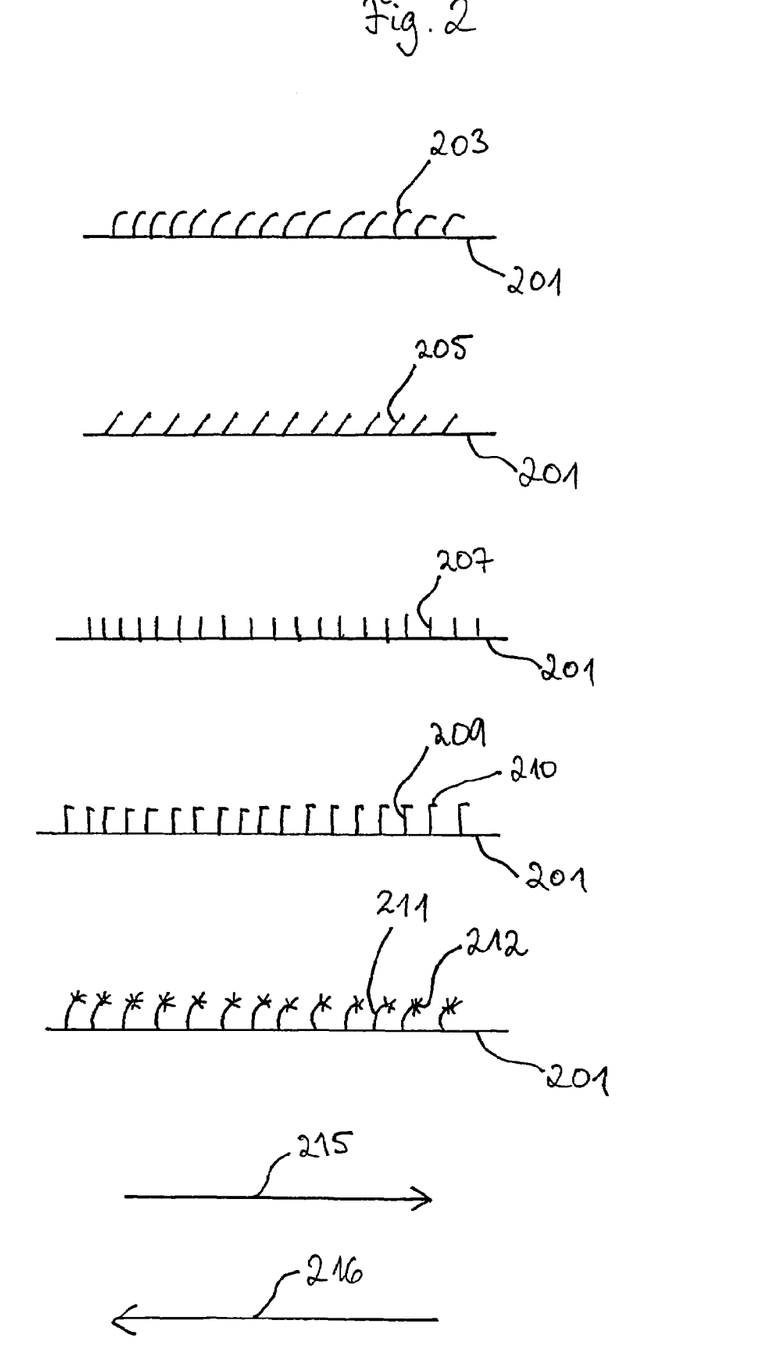
FIG. 2 shows various embodiments of microstructure elements.

FIG. 2 shows a diagrammatic illustration of various embodiments of microstructure elements. Those microstructure elements are of a radial extent beyond the surface of the electrode line, said extent being a fraction of the electrode line diameter. The microstructure elements are adapted to counteract displacement of the electrode line in the longitudinal direction, when they are in contact with a vessel wall.

Provided on the electrode line surface 201 are for example microstructure elements 203 which are in the form of curved microbristles. The microbristles 203 are curved with a directional component facing in the proximal direction 215. As a result, upon displacement of the electrode line in the proximal direction 215, the microbristles 203 produce an increased level of resistance to displacement of the electrode line in the distal direction 216.

The microbristles can also be in the form of straight microbristles 205. These straight microbristles 205 are arranged at a predetermined angle relative to the surface 201 of the electrode line, in such a way that they have an orientational component in the proximal direction 215.

The microbristles 207 are also straight and are arranged in perpendicular relationship to the electrode line surface 201.

That provides for an equally high level of resistance upon displacement of the electrode line in the proximal direction 215 and in the distal direction 216.

The microbristles 209 are disposed on the electrode line surface 201 and, at the end remote from the electrode line surface 201, have a hook 210 which is shaped in the proximal direction 215. The hook 210 is adapted to engage into a vessel wall upon displacement of the electrode line in the proximal direction 215 and thereby to produce a particularly high level of resistance to displacement of the electrode line in the proximal direction 215.

The microbristles 211, like the microbristles 203, are also curved in the proximal direction 215 and, at the end remote from the electrode line surface 201, have a star-shaped branching configuration 212. By virtue of that configuration, upon coming into contact with a vessel wall, the microbristles 211 can particularly effectively engage into same and thereby produce a high level of resistance to displacement of the electrode line in the proximal direction 215.

Figure 3:
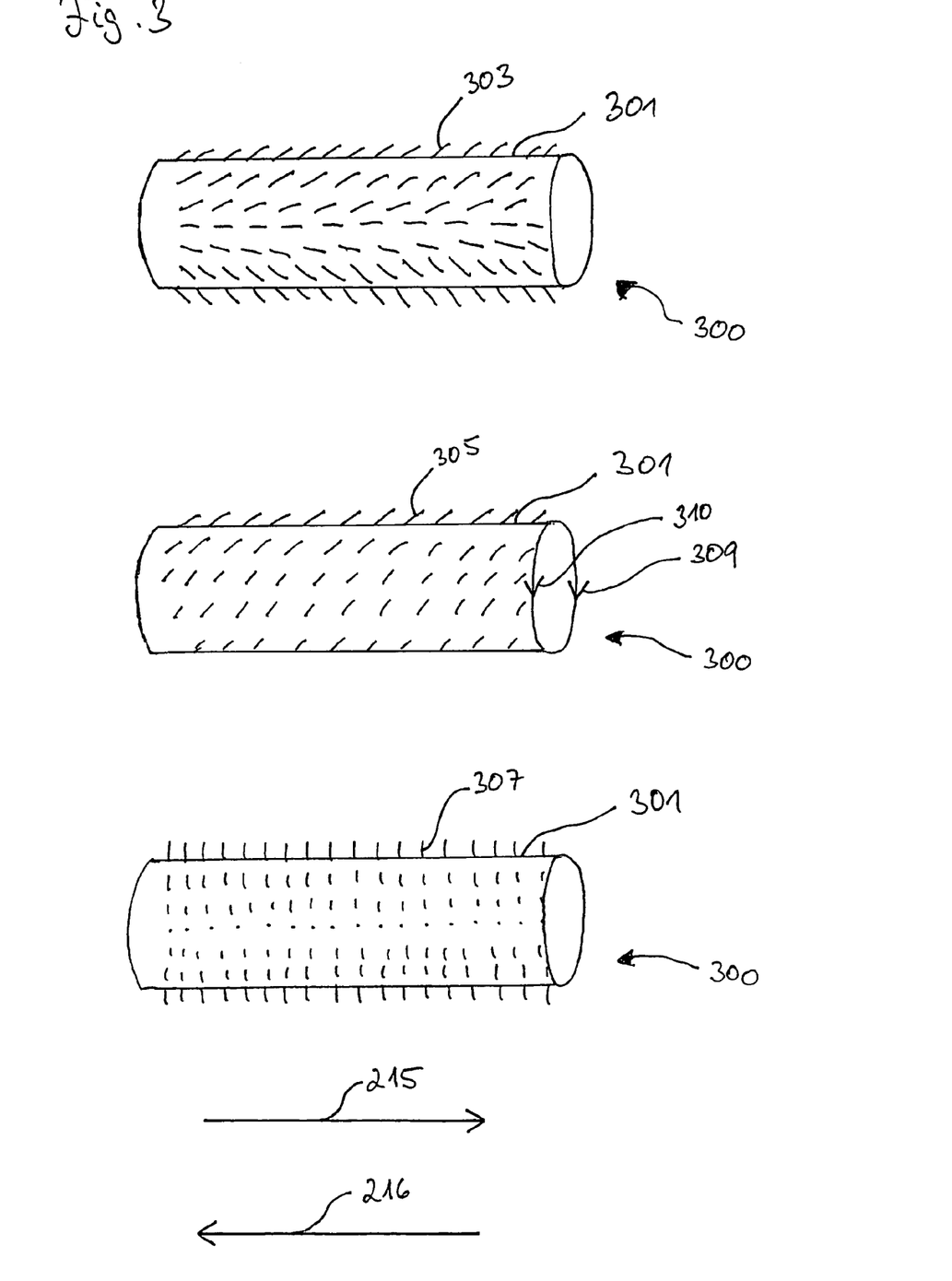
FIG. 3 shows an arrangement by way of example of microbristles on an electrode line.

FIG. 3 diagrammatically illustrates an embodiment by way of example of microbristles on an electrode line. FIG. 3 illustrates portions of an electrode line 300, on the electrode line surface 301 of which are disposed microbristles. The microbristles 303 are oriented at a predetermined angle relative to the electrode line surface 301 with a directional component in the proximal direction 215.

In a further example microbristles 305 are arranged at a predetermined angle relative to the electrode line surface 301 and are oriented with a directional component in the proximal direction 215. The microbristles 305 are also oriented in respective mutually parallel relationship at a predetermined angle relative to the longitudinal axis of the electrode line so that, upon rotational movement of the electrode line in the peripheral direction 309 the microbristles 305 are anchored in a vessel wall when in contact therewith. Upon rotational movement of the electrode line in the direction 310 opposite to the peripheral direction 309 the microbristles 305 can be released from the condition of being anchored in the vessel wall again.

The microbristles 307 are arranged orthogonally on the electrode line surface 301. By virtue of that arrangement, an equally high level of resistance is opposed to displacement movement upon displacement of the electrode line in the proximal direction 215 and also upon displacement of the electrode line in the distal direction 216.

Figure 4:
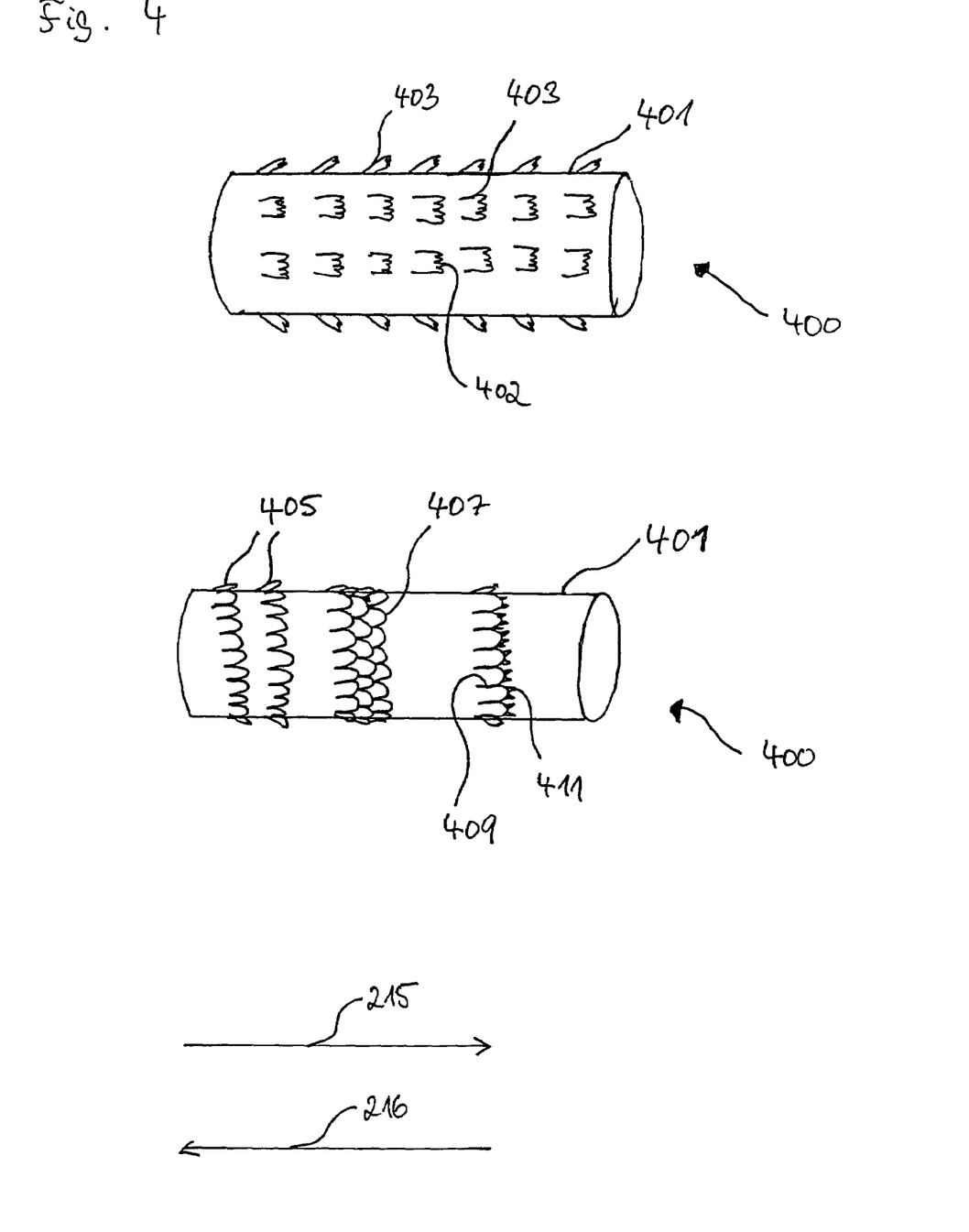
FIG. 4 shows portions of an electrode line with various embodiments of microstructure elements which are in the form of scales.

FIG. 4 diagrammatically shows portions of an electrode line 400 with various embodiments of microstructure elements which are in the form of scales. The embodiments illustrated in FIG. 4 are shown in part jointly on one electrode line portion. An electrode line may have a respective one of the illustrated alternative configurations or a combination of various alternative configurations.

The scales 403 are oriented at a predetermined angle relative to the electrode line surface 401 in the proximal direction 215. The scales 403 have an edge which extends in perpendicular relationship to the longitudinal axis of the electrode line and which has a toothed configuration 402. That toothed configuration is adapted to particularly effectively engage into a vessel wall and be anchored therein, upon displacement of the electrode line in the proximal direction 215.

In a further example, scales 405 with a round edge are arranged in mutually juxtaposed relationship extending around an electrode line in the peripheral direction thereof. The scales 405 form rings on the electrode line surface 401, which are spaced from each other. Shown further to the right on that portion is an embodiment in which scales 407 with a rounded-off edge are arranged in such a way that scales which occur in succession in the longitudinal axial displacement are respectively displaced relative to each other in the peripheral direction by half a scale width. Also arranged on the portion in the peripheral direction in mutually juxtaposed relationship are scales 409 with a round scale edge, wherein the scale edge has prongs 411 which are oriented in the proximal direction 215 at at least one edge portion extending in the peripheral direction. Alternative configurations (not shown) of an electrode line can include a respective one of the alternative scale configurations 405, 407 or 409. A combination of the alternative scale configuration 409 with the alternative scale configuration 407 on one electrode line or a combination of the alternative scale configuration 409 with the alternative scale configuration 405 on one electrode line are possible alternative embodiments.

Figure 5:
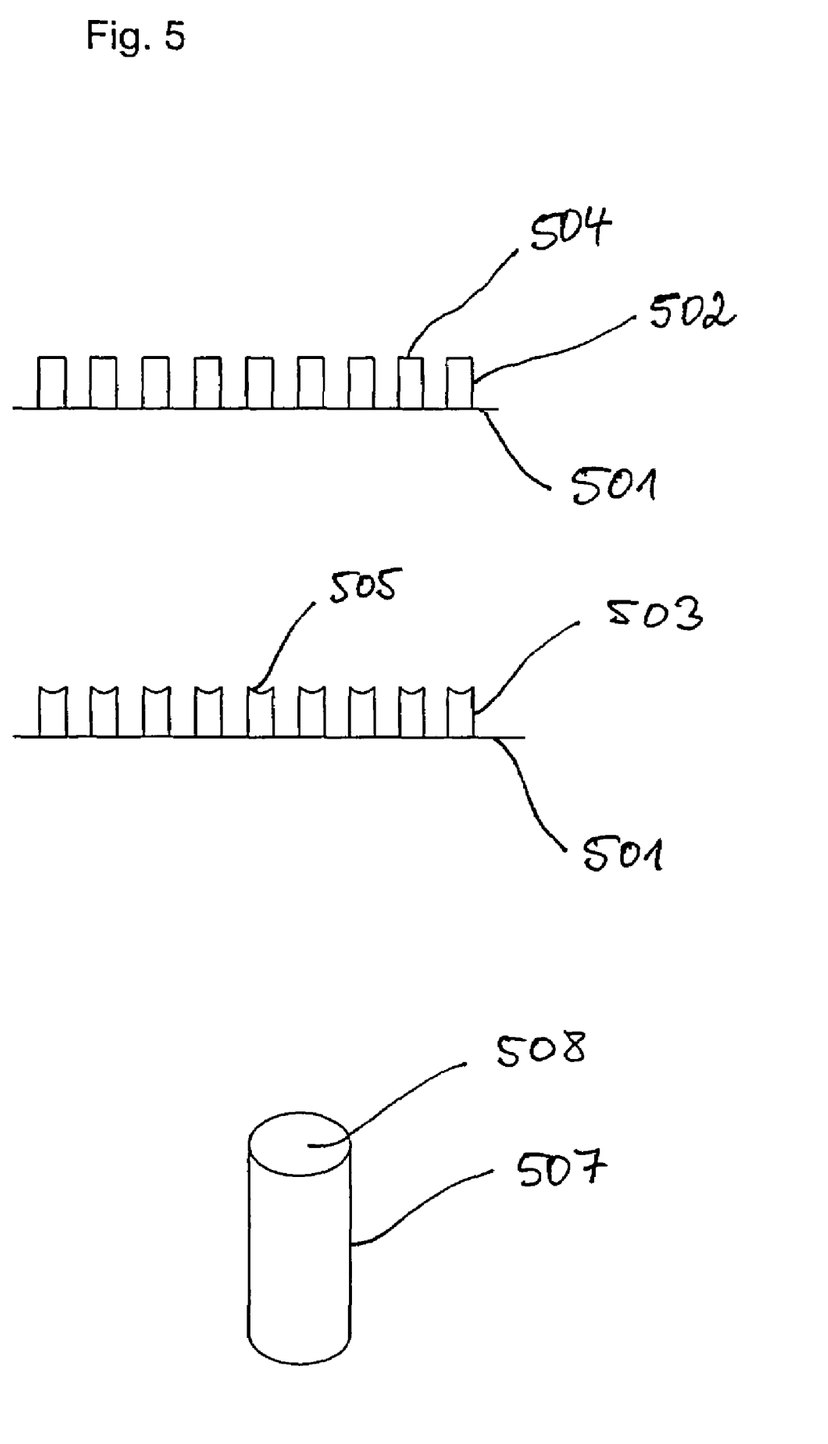
FIG. 5 shows diagrammatically illustrated embodiments of knobs.

FIG. 5 diagrammatically illustrates embodiments of knobs. The knob embodiments 502 and 503 are disposed on an electrode line surface 501 and in this example are diagrammatically illustrated in a side view as a section.

The knob 507 is in the form of a portion of a cylinder and has a circular adhesion surface 508 which is adapted to cling to a vessel wall by adhesion.

The knobs 502 and 503, like the knob 507, can be of a cylindrical configuration. In the case of the knob shape 502 the adhesion surface 504 is flat. In the case of the knob 503 the adhesion surface 505 is of a concave shape and is thus in the form of a suction cup.

In a variant design (not shown), as an alternative to the circular shape, the adhesion surface can also be in the form of a polygon.

An electrode line in accordance with various embodiments of the present invention can have a combination of surface regions which extend entirely therearound or which do not extend entirely therearound, with any respective combination of the above-indicated alternative configurations of microstructure elements in the form of microbristles, scales or knobs.

Figure 6:
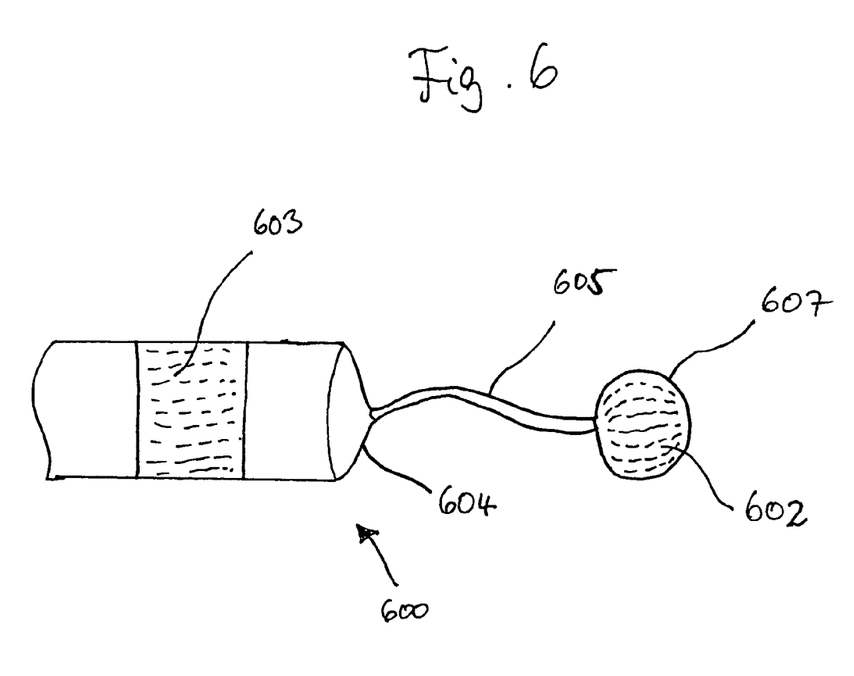
FIG. 6 shows an embodiment in which an electrode head is cord-connected to a distal end of an electrode line by way of a connecting line.

A further development of the invention is diagrammatically illustrated in FIG. 6. In this embodiment an electrode head 607 is cord-connected to the distal end of an electrode line by way of a connecting line 605. In the region of the distal end 600 the electrode line has a surface region 603 with a microstructure. In this example the surface region 603 is of such a nature as to extend around the electrode line in the peripheral direction. In this embodiment the connecting line 605 is sealed off in relation to the electrode line body at the distal end thereof by a sealing mass 604, for example a silicone sealing mass. Both the electrode 607 and also the surface region 603 at the distal end 600 of the electrode line have a microstructure 603 formed by microstructure elements. The microstructure elements of the microstructure 602 are preferably of an electrically conductive nature, for example the electrode head 607 may contain the electrode line material and have a gold or platinum layer at the surface thereof. The gold or platinum layer can be applied by vapor deposition or sputtering. This embodiment advantageously permits a relative movement along the longitudinal axis of the electrode line between the electrode head 607 and the distal end 600 of the electrode line. The microstructure elements of the microstructures 602 and 603 can be embodied in the form of microbristles, knobs or scales in one of or a combination of the above-described embodiments and arrangements. In an alternative embodiment (not shown) the electrode line, similarly to FIG. 6, has an electrode head which does not have any microstructure. The electrode head is thus in the form of a freely floating electrode, preferably in the form of a ventricular electrode.

In a development of the invention the microstructure of the surface region of the electrode line is such that body tissue can grow into the surface region.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An implantable electrode line comprising:
   a proximal end;
   a distal end;
   an outer electrode line surface; and
   an electrode line longitudinal axis,
   wherein the electrode line in a region of the distal end includes a surface region with a microstructure, the surface region being provided for lateral contact with a vessel wall and being arranged at a spacing relative to the distal end which measures a plurality of electrode line diameters, and wherein the microstructure is formed by a plurality of microstructure elements which are arranged on the electrode line surface and which are distributed over the surface region both in a longitudinal direction and also, in a peripheral direction and which have a component extending radially, wherein the microstructure elements are of a radial extent which is a fraction of the electrode line diameter and are adapted, upon contact with a vessel wall, to counteract displacement of the electrode line along the electrode line longitudinal axis,
   and wherein the microstructure elements are in the form of knobs which are adapted to cling to a vessel wall by adhesion and wherein the knobs are in the form of suction cups.

2. An implantable electrode line comprising:
   a proximal end;
   a distal end;
   an outer electrode line surface; and
   an electrode line longitudinal axis,
   wherein the electrode line in a region of the distal end includes a surface region with a microstructure, the surface region being provided for lateral contact with a vessel wall and being arranged at a spacing relative to the distal end which measures a plurality of electrode line diameters, and wherein the microstructure is formed by a plurality of microstructure elements which are arranged on the electrode line surface and which are distributed over the surface region both in a longitudinal direction and also in a peripheral direction and which have a component extending radially, wherein the microstructure elements are of a radial extent which is a fraction of the electrode line diameter and are adapted, upon contact with a vessel wall, to counteract displacement of the electrode line along the electrode line longitudinal axis,
   and wherein the microstructure elements are in the form of scales with a scale edge, and wherein the scales have at least one prong at the scale edge.

3. The implantable electrode line as set forth in claim 2 wherein the scales are arranged at a predetermined angle relative to the electrode line surface in such a way that the scale edge is spaced from the electrode line surface.

4. The implantable electrode line as set forth in claim 3 wherein the scales are arranged in such a way that at least one edge portion of the scale edge has an orientational component extending in perpendicular relationship to the electrode longitudinal axis.

5. The implantable electrode line as set forth in claim 4 wherein the scales have at least one prong at the scale edge.

6. The implantable electrode line as set forth in claim 3 wherein the scales have at least one prong at the scale edge.

* * * * *